United States Patent [19]
Meyer et al.

[11] 4,283,128
[45] Aug. 11, 1981

[54] PHOTOMICROGRAPHIC SYSTEM FOR FLOWING FLUIDS

[75] Inventors: Raymond A. Meyer, Newbury Park, Calif.; Frank J. Freestone, Edison, N.J.

[73] Assignee: The United States of America as represented by the Administrator of the U.S. Environmental Protection Agency, Washington, D.C.

[21] Appl. No.: 161,990

[22] Filed: Jun. 23, 1980

[51] Int. Cl.³ .................. G01T 1/167; G03B 17/48
[52] U.S. Cl. .................................... 354/79; 250/301
[58] Field of Search ............ 354/79; 350/19; 356/36; 250/301, 335

[56] References Cited

U.S. PATENT DOCUMENTS

| | | | |
|---|---|---|---|
| 1,021,229 | 3/1912 | Baldus | 73/57 |
| 2,524,926 | 10/1950 | Peery | 356/23 |
| 2,956,489 | 10/1960 | Carter | 354/79 |
| 3,275,834 | 9/1966 | Stevens | 250/218 |
| 3,390,229 | 6/1968 | Williams | 358/107 |
| 3,422,443 | 1/1969 | Jansen | 346/107 |
| 3,510,648 | 5/1970 | Leger | 250/301 X |
| 3,659,940 | 5/1972 | Hansen et al. | 356/36 |
| 3,706,495 | 12/1972 | Doton | 356/28 |
| 3,710,111 | 1/1973 | Collura | 250/301 X |
| 3,917,945 | 11/1975 | Sema et al. | 250/301 |

Primary Examiner—Donald A. Griffin

[57] ABSTRACT

A photomicrographic system for measuring the number, size distribution and movement rate of foreign matter, e.g., droplets in a flowing liquid stream comprises a microscope having a field of view and an optical axis, along which lie an objective lens and a viewing lens, said microscope being disposed such that the plane of its optical axis is horizontal; a liquid sample cell disposed within the field of view of said microscope; a solenoid valve located downstream of said sample cell and connected thereto, whereby the liquid flow through the cell may be stopped or started; a standpipe pressure regulator fed by the flowing liquid stream and connected at its low pressure end to said sample cell, whereby a steadily flowing sample stream at essentially constant pressure is provided at the entrance of the sample cell; a flash illuminator disposed such that a flash therefrom illuminates said sample cell; and a camera disposed such that the image of said cell formed at the viewing lens of said microscope forms the film image of said camera, the latter being provided with a motor driven film winder.

10 Claims, 6 Drawing Figures

PHOTOMICROGRAPHIC SYSTEM FOR FLOWING FLUIDS

BACKGROUND OF THE INVENTION

There are many situations in which it is necessary and/or desirable to determine the characteristics and quantity of foreign matter which is entrained, in a liquid system. Such a determination is particularly difficult when flowing liquid-liquid or liquid-gas systems are involved, especially those which are subjected to turbulence, since the foreign matter, liquid or gas, if immiscible in the flowing liquid stream, is usually emulsified, suspended or otherwise dispersed in the form of droplets of varying sizes. Sufficient characterization of such dispersed impurities thus requires a measurement of droplet number distribution, droplet size distribution, droplet composition distribution, as well as other parameters such as droplet densities, etc. Heretofore, such measurements have not been possible on a commercial scale.

One area particularly sorely in need of such measurement capability is offshore oil well technology. During the pumping of oil from sea-based platforms, a quantity of brine is unavoidably obtained along with the desired oil. This brine is referred to as "produced water". Because of its presence, the problem exists to remove the water from the oil generally by gravity separation or flotation.

In turn, such separation procedures make very desirable techniques for determining the quality of the oil-/water separation on as quantitative a basis as possible. Since the oil/water mixture is blown through a small orifice during the pumping procedure, and since high velocities are required in the pipelines to maximize throughput, the oil is very greatly dispersed in the water by the high shear forces which are created. Accordingly, this quantifying of the quality of the oil/water separation becomes a problem of characterizing the oil droplet distribution within the produced water.

The problem is exacerbated by the existence of gas bubbles in the oil/water emulsion. In addition, solid matter is often also entrained. Accordingly, it is not only necessary to characterize the properties of the oil droplets in the flowing water, but it is also necessary to distinguish such droplets from similarly sized and shaped gas bubbles and other matter.

The characterization of the oil distribution within the water is further complicated by the fact that the flowing liquid stream is generally under relatively high pressure which may vary within a wide range, e.g., about 1 to 100 psig. Accordingly, any measurement system must be capable of sampling the liquid stream within this entire range, preferably on a continuous basis. Furthermore, in order to ensure reliability, the sampling operation itself must not perturb the characteristics of the oil droplets which are being measured.

SUMMARY OF THE INVENTION

Accordingly, it is an object of this invention to provide an apparatus and method for measuring the properties of moving foreign matter, gaseous or liquid, e.g., droplets, within a liquid-liquid or liquid-gas flow, thereby providing accurate and reliable data and fulfilling the aforementioned requirements.

Upon further study of the specification and appended claims, further objects and advantages of this invention will become apparent to those skilled in the art.

In one aspect of this invention, these objects have been attained by providing a photomicrographic system for measuring the number, size distribution and movement, e.g., rise, rate of foreign matter particles, gas bubbles or droplets in a flowing liquid-liquid or liquid-gas stream, comprising:

a microscope having a field of view and an optical axis, along which lie an objective lens and a viewing lens, said microscope being disposed such that the plane of its optical axis is horizontal;

a liquid sample cell disposed within the field of view of said microscope;

a solenoid valve located downstream of same sample cell and connected thereto, whereby the liquid flow through the cell may be stopped or started;

a standpipe pressure regulator fed by the flowing liquid stream and connected at its low pressure side to said sample cell, whereby a steadily flowing sample stream at essentially constant pressure is provided at the entrance of the sample cell;

a flash illuminator disposed such that a flash therefrom illuminates said sample cell; and a camera disposed such that the image of said cell formed at the viewing lens of said microscope forms the film image of said camera, the latter being provided with a motor driven film winder.

In another aspect of this invention, these objects have been attained by providing a method of measuring the number, size distribution and movement rate of foreign matter entities in a flowing liquid-liquid or liquid-gas stream comprising:

permitting said flowing liquid to flow through said standpipe, cell and solenoid valve of the photomicrographic system described above;

stopping the flow of said flowing liquid through said cell by closing said solenoid valve, thereby enclosing a sample of said liquid in said cell, thereby enclosing part of said sample having entrained foreign matter entities within the field of view of said microscope;

prior to the movement of the foreign matter entities to be measured from said field of view, taking a first photomicrograph of said liquid sample under the illumination of a first light flash from said flash illuminator, thereby obtaining a first photomicrograph of said foreign matter entities in that portion of said cell which is within the field of view of said microscope;

prior to the time at which the thus-photographed foreign matter entities move out of said field of view, taking at least one additional photomicrograph of said foreign matter entities, at predetermined time intervals from the taking of said first photomicrograph;

measuring the number, size and position of said foreign matter entities in said photomicrographs; and from the change in position of each of said photographed foreign matter entities during each of said predetermined time intervals as measured from said photomicrographs, determining the movement rate of each of said foreign matter entities.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same of similar parts throughout the several views, and wherein.

DETAILED DISCUSSION

Using the method of this invention in conjunction with the apparatus of this invention, a series of time-lapse photomicrographs of foreign matter, e.g., of rising droplets is taken. The first photomicrograph is taken shortly after the solenoid valve is closed, thereby trapping a liquid sample within the confines of the sample cell. Before the droplets whose photomicrograph has been taken have reached the top of the field of view of the optical system, additional photomicrographs are taken, thereby providing a time record of the rise of the droplets, air bubbles and other entrained matter. Of course, the oil drop or other dispersed minor component undergoes vertical movement only when its density is different than that of the base liquid. The extent of this vertical movement between photographs and the size of each particle may be determined by manual or automatic measurement of each film image. From this data, Stokes' Law calculations can be used to determine the density of each particle, given the other available measured particle and stream parameters which are thereby required.

From the density of each particle, those which are composed of oil, those which are composed of gas, those which are composed of gas/oil mixtures, and those which are composed of other minor components can be readily determined. Since the measurement system, including the size of the cell within the field of view and other relevant parameters, will be accurately calibrated, from the number and size distribution of the particles and the identity of the composition of each, the impurity composition of the liquid flowing stream can be accurately determined. Since the entire apparatus of this invention can be readily integrated into a portable, self contained, fully automated apparatus capable of field use, this invention provides an on-site capability of determining the quality of purification of a liquid stream on a continuous basis.

As can be seen, the present invention provides an accurate and reliable method of analyzing the dispersed impurity content of a flowing liquid. Non-spherical suspended material, by its shape per se, can be readily recognized as not being oil in a water/oil emulsion. Furthermore, material of biological origin, e.g., shells, can also be readily recognized by its shape, as can gas bubbles by their densities. The invention also provides a permanent record of the impurity content. Furthermore, a wide dynamic range of impurity sizes, e.g., 2–100 micrometers, can be measured in a single system setting.

Figure 1:
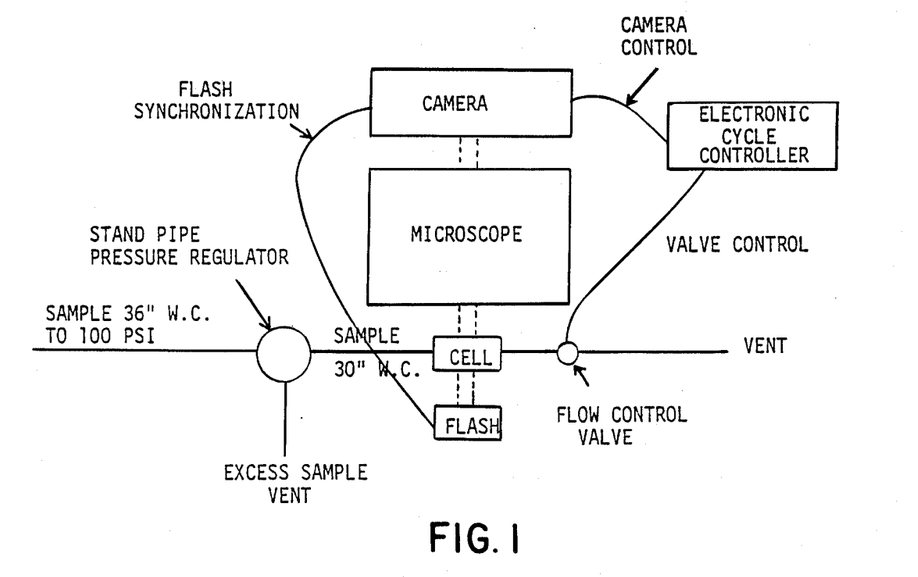
FIG. 1 is a block diagram of one embodiment of the key components of the apparatus of this invention.
Figure 2:
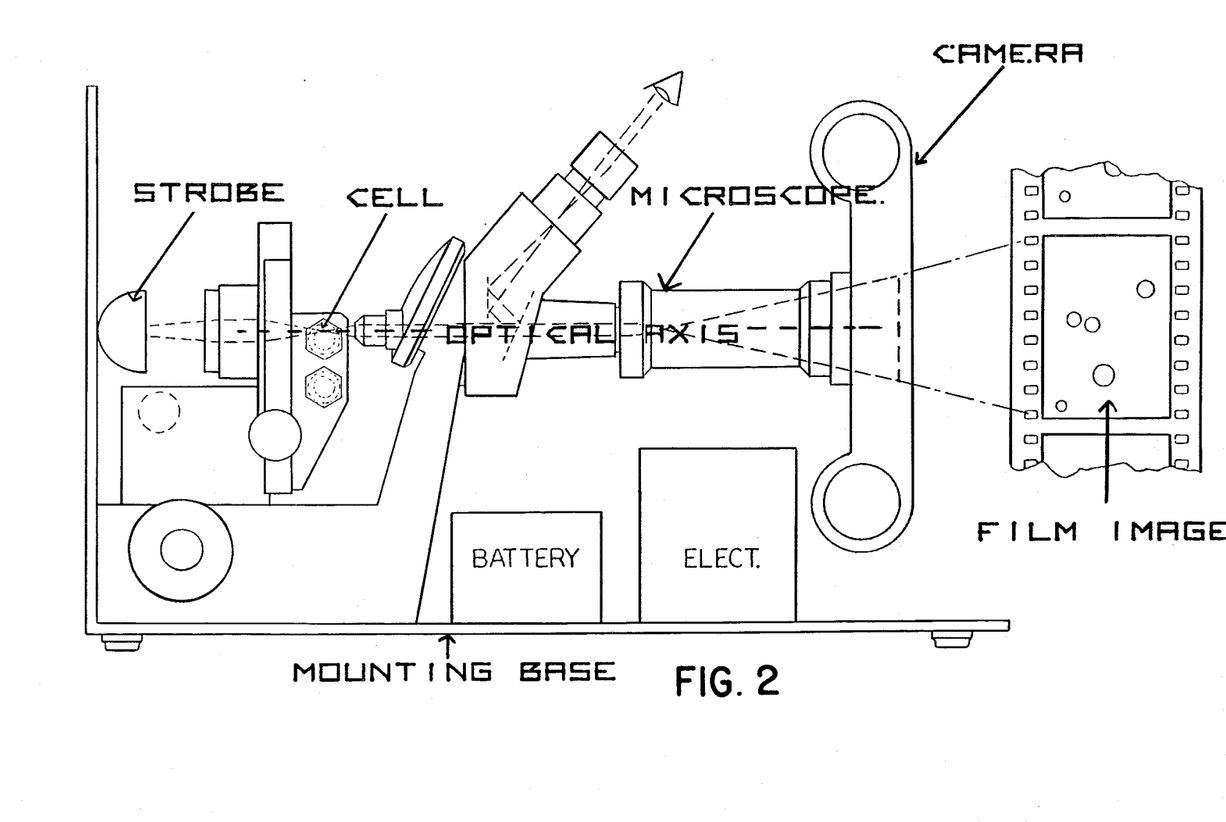
FIG. 2 schematically illustrates a side view of key components of the apparatus of this invention.

In order for the system of this invention to function properly, it is necessary that the water sample be briefly at rest in the microscope cell while the photomicrographs are being taken (see FIGS. 1 and 2). Moreover, this must be accomplished in such a manner that no perturbing forces are introduced on the liquid sample which is being measured since these would alter the parameters being measured, thereby providing inaccurate and unreliable results.

Figure 3:
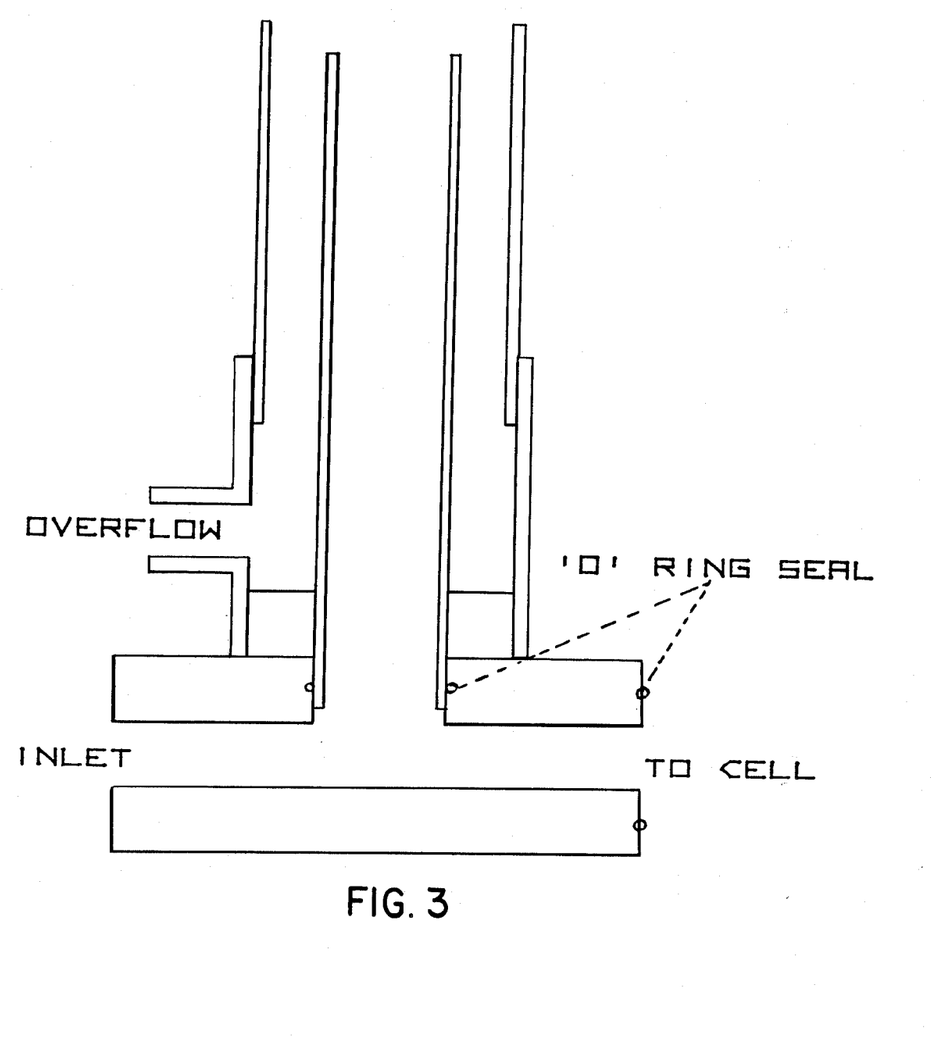
FIG. 3 schematically illustrates one embodiment of the standpipe pressure regulator utilized in the apparatus of this invention.

Accordingly, the liquid from the high pressure stream is lead through a standpipe pressure regulator prior to its entry into the sample cell of the microscope. A typical embodiment of such a standpipe pressure regulator is shown in FIG. 3. Any conventional standpipe pressure regulator can be employed which is system compatible. As a result of this component, the excess high pressure liquid flow exits from the standpipe and only a steady, essentially constant pressure flow reaches the sample cell. The typical pressure range entering the standpipe regulator is about 1.5–7 psig (flow rates of 1–200, preferably 1–15 l/min), while typical pressures leaving the standpipe and entering the sample cell are about 0.4 psig (flow rates of about 1 l/min). The various dimensions of the standpipe and connecting tubing, etc. can be chosen in accordance with conventional considerations for a given system, e.g., input pressure, desired output pressures etc.

This standpipe pressure regulator achieves a pressure reduction and an even flow of liquid sample despite the normally large pressure fluctuations within the flowing liquid and the wide range of pressures which must be accepted by the system. Most importantly, it achieves this effect without the introduction of any extraneous sheer forces into the flowing liquid sample which would perturb the real number and size distribution of the droplets or other foreign matter to be measured. Further in this regard, the momentary interruption of the flow of the liquid through the sample cell is achieved by the closing of a solenoid valve downstream of the liquid cell (FIG. 1). In this way, any shear forces which would be introduced into the liquid stream during the closing of this valve will not affect the measurement of the properties of the liquid within the cell. This is further achieved by waiting a predetermined amount of time from the valve closing to the taking of the first photograph.

The closing of the valve initiates a sequence of events by which a series of photomicrographs is taken of the moving foreign matter, e.g., rising droplets, within the sample cell. As mentioned above and as can be seen from the following detailed examples, a short rest time is usually taken after the valve is closed, e.g., 4–15 seconds, prior to the commencement of the taking of photomicrographs. Thereafter, the timing of photomicrographs is controlled by a conventional electronic controller, e.g., a computer, which determines when the first photograph is taken after the rest period, i.e., the flash illuminator is flashed, the camera shutter is opened and the image taken, whereafter the automatic film advance is actuated. The requirements of the particular systems being measured will determine the number and timing of subsequent flashings i.e., generally about 3 photographs are taken. For the specific application of this invention to the measurement of an oil drop dispersion in produced water, the initial photograph has been taken after a four second rest time and is followed by subsequent photos at intervals of 0.3 and 1.7 seconds after the first photograph.

After completion of a series of sequential photomicrographs, the automatic electronic controller reopens the solenoid valve and the liquid flow is permitted to continue until a new sample corresponding to the instantaneous characteristics of the flowing liquid in the standpipe is flowing through the cell. The dimensions and other details of the particular embodiment determine the flow period required to provide a fresh sample. In one embodiment it was four seconds.

The measurement capabilities of the system of this invention are variable and depend upon the properties of the system to be measured, as well as the optical resolution capabilities of the microscope flash illuminator and camera, all of which can be chosen at will as long as they are compatible with one another and the system requirements.

The microscope of the system of this invention is disposed with its viewing axis horizontal so that the vertical movement within the sample cell occurs across the face of the field of view of the optical system. Of course, any other optical system which performs a function equivalent to that of the microscope of the system described herein is also included within the scope of this invention. This is also true of any of the other components of the apparatus of this invention.

As a result of the operation of the sampling system of this invention, i.e., the standpipe in combination with the cell and solenoid valve, turbulent flow is maintained throughout the system until the sampling occurs so that the foreign matter entities of interest, e.g., droplets will be uniformly dispersed within the liquid. Of course, simultaneously, while the inherent turbulence of the system is maintained, no additional sheer forces are introduced. Were a more conventional valve sampling system employed, such extraneous sheer forces would be introduced, thereby destroying the inherent characteristics of the system. The standpipe is utilized since the pipeline sample port is essentially never a controllable portion of the system in terms of pressure regulation. However, in order to minimize shear within the valve which feeds the flowing stream from the pipeline into the standpipe, it is preferred that a ball or gate pipeline valve be utilized. In any case, the valve is completely open during all of the subsequent sampling operations. In general, the techniques of sampling should obey the tenets set forth by Rushton and Hilestad, "Sampling of Nonhomogeneous Flow in Pipes", API proceedings 44, 3, pp. 517–534, 1964; and Karabelas, "Recent Studies Improve Velocity Criteria Used for BS&W. Sampling", Oil and Gas Journal, Apr. 17, 1978, pp. 99–104.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A system was designed to sample from sources having pressures of 1.3–100 psig. Fifty feet of ⅝ inch plastic garden hose was used to conduct the sample from the upper deck sampling point of an off-shore platform to the next lower deck, an estimated 15 foot drop. Flow in this hose was turbulent with a Reynolds number of $1.7$–$2.0 \times 10^4$. The 10–12 l/min flow from the transfer hose entered the standpipe pressure regulator as shown in FIG. 1.

Figure 4:
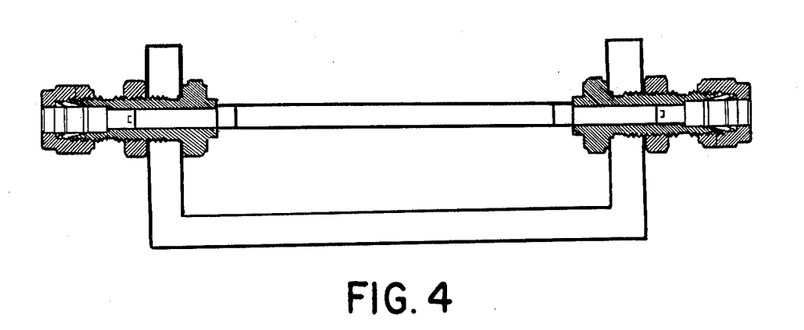
FIG. 4 illustrates one embodiment of a microscope cell which can be used within the scope of this invention.

The sample inlet to the cell was maintained at a constant pressure by a unique application of the standpipe principle (FIG. 3). Valves and pressure regulators could not be used because of flow shear induced sample alteration. The standpipe allowed for a wide range of sample pipeline pressures while maintaining a supply of fresh sample at constant pressure to the cell inlet. The outer tube of the standpipe was 3 inch plastic drain pipe. The inner tube was a 1½ inch plastic pipe. From the bottom of the lower tee to the top of the outer pipe was 37 inches; the top of the inner pipe was located 2 inches below the top of the outer pipe. The connecting line between the bottom tee of the standpipe and the sample cell was ½ inch tubing. Sample in excess of that required by the photomicrographic system overflowed the center standpipe and was returned to the drain system. Flow through the standpipe-microscope connector tube and cell was 60 cc per 4 seconds, or 900 cc/min. This flow volume was sufficient to clear all the sample from the previous cycle and supply sample fresh from the standpipe to the cell. The Reynolds numbers for flow in the connecting tube and cell were $2.7 \times 10^3$ and $6.8 \times 10^3$, respectively. The microscope cell was fabricated from a $1 \times 0.1$ cm Vitrodynamics slide cemented into ⅛ inch Swagelok fittings. See FIG. 4. It was of unique design to provide free, turbulent sample movement as well as a long rise path required to measure the oil drop density. The inside of the cell was 10 mm high and 1 mm thick, which, of course, is nontypical of the standard microscope cell. The exterior cell length was 5.1 cm.

An Olympus BH Series microscope with a trinocular tube was unaltered. An FK 6.7× photo eyepiece and a 10× planachromatic objective were selected to produce nominal photographic magnification of 150×. The microscope illumination was via a stroboscopic light source such as a Sun Pak 611 electronic flash or Strobotac 1543 which requires a smaller battery and has a shorter flash duration (5 μsec.). An Olympus OM 1 35 mm camera with a motor drive and a 250 exposure back were also unaltered, and connected to the microscope with a simple photomicro adapter. (See illustration of FIGS. 1 and 2.) The microscope is operated "on its back" with the viewing axis horizontal rather than vertical as is normal practice. This innovation causes vertical movement within the cell to appear as transverse motion on the camera film and allows measurement of the particles' rise or fall.

The microscope base was securely fastened to the base of an aluminum housing which would withstand pressurization to several psig. The housing also contained the operational battery and electronic timer system. Nitrogen was used to purge and pressurize the housing to meet requirements for operation in National Electric Code Class 1, Division 1, Group D atmospheres. A pressure-activated safety switch precluded operation when internal pressure approached atmospheric.

The standpipe/cell/solenoid system delivered a uniformly dispersed, uncompromised flowing sample to the microscope cell. The sample properties, of course, determined the characteristics of the time lapse photomicrography. The linear flowrate through the cell was $1.7 \times 10^6$ microns per second. An arbitrary standard of 0.1 micron movement during photography was adopted to assure image clarity. This standard requires a maximum exposure duration of 60 nanoseconds. The state-of-the-art electronic flash units deliver 500 nanosecond flashes and the commonly used photographic units are rated at 50 microsecond duration. Hence photography of the flowing sample was impossible. Slowing the flow would compromise sample integrity. Stopping the flow could be equally destructive to sample integrity unless timing was established with care and the system designed as per this invention to minimize perturbations on the sample. The long dimension, 1 cm, of the microscope cell was vertical, and the microscope was focused near the top of the cell. The camera was operated with its long axis vertical and a photograph recorded a 535×349 micrometer area. The typical sample parameters shown in Table 1 were chosen as a basis for calculation.

TABLE 1

| CHARACTERISTICS OF OILY WATER | |
|---|---|
| Oil Density | 0.8650 gm-ml$^{-1}$ |
| Water Density | 1.025 gm-ml$^{-1}$ |
| Water Viscosity | .01025 poise |
| Acceleration Due to Gravity | 980 cm-sec$^{-2}$ |

Terminal velocity was reached in a few milliseconds and the Stokes' law rise rate calculation could be reduced to Eq. 1 (Manual on Disposal of Refinery Wastes; Volume on Liquid Wastes, Ch. 5-Oil-Water Separtator Process Design, Appendix 1, A.P.I., Washington, D.C.) whose disclosure is incorporated by reference herein).

$V(\text{micron sec}^{-1}) = .5182 * D^2 \text{ (microns)} \times$
[density of water − density of oil]
(D = droplet diameter)

A three-photograph-per-water-sample scheme was chosen to optimize data quality and collection. This sequence is summarized in Table 2 below.

TABLE 2

| TIMING SEQUENCE (SECONDS) | |
|---|---|
| $T_o$ | Open solenoid flow control valve |
| T + 4.0 | Close solenoid flow control valve |
| T + 8.0 | First camera operation* |
| T + 8.3 | Second camera operation |
| T + 9.7 | Third camera operation |
| T + 10.0 | Reset and restart pulse |

*Flash is synchronized by the camera shutter and film advance is controlled by the camera motor.

The first photograph, taken 4 seconds after flow interruption, was considered zero time; the second was taken 0.3 second later and the third, 1.7 seconds after the first. The movement (calculated by Eq. 1) of several different diameter oil drops during these periods is shown in Table 3. The 5.7 second period is total time between flow interruption and the last photograph.

TABLE 3

| OIL DROP RISE | | | |
|---|---|---|---|
| | Calculated Movement | | |
| Diameter (m) | 0.3 Second (microns) | 1.7 Seconds (microns) | 5.7 Seconds (microns) |
| 2 | 0.1 | 0.6 | 1.9 |
| 10 | 2.5 | 14 | 47 |
| 20 | 10 | 56 | 189 |
| 50 | 62 | 352 | 1181 |
| 75 | 140 | 793 | 2658 |
| 100 | 249 | 1409 | 4725 |
| 150 | 560 | 3171 | 10633 |

For accuracy in use of the system, as in any photographic measurement technique, accurate calibration is required. One method is illustrated below.

The size of the microscope viewing cell determines the liquid volume in focus. It is defined by the magnification, length and width of the film and the depth of focus of the objective. Under the conditions used in this example, the cell dimensions were 535×349 microns. The apparent depth focus was dependent on the drop diameter.

A slide of oil drops captured in gelatin was photographed with the same color film and electronic flash used in this field study example. The microscope stage was moved in 4 micron steps over a wide range with photographs taken at each step. Twelve drops were selected ranging in size from 2 to 115 microns in diameter, and the range of sharp image photographs was determined by inspection. The data were fitted to various equations using conventional statistics programs, e.g., an HP 9815 program. Equation 2 shows the best fit.

Depth of Focus (μm) = 3.861 +  (2)
(5.088 × Natural Logarithm of Diameter (μm))

This equation may only be applied under the exact conditions used in its determination, including, for example, the type of film, e.g., color vs. black and white. Of course, for any other selected system, equivalent equations can be determined by similar routine, preliminary experiments and calculations.

In this experiment, the determination of "in focus" was found to be very subjective and the data analyst was well trained by inspection of the calibration photographs. Retraining was performed at periodic intervals to eliminate subjective drift. There was a marked tendency to "find" drops in sparsely populated exposures which led to high drop counts and oil contents. The retraining minimized this effect. Once the concept and requirements of the viewing cell as a boundaryless volume of water sample located someplace within the glass cell is established, the preferred location may be selected. The objective side of the viewing cell is typically located 200 microns into the liquid to minimize the effect of the cell wall on drop rise. The top of the viewing cell is a nominal 1500 microns below the top of the microscope cell to avoid optical distortion from the cell curvature (See FIG. 4). If a 1000 micron section at the bottom of the cell is discounted, the drops may be said to have a conservative rise path of 7000 microns to the bottom of the 535 micron high viewing cell.

As stated above, the sampling procedures place an uncompromised and uniformly dispersed sample within the microscope cell when flow is interrupted. It is shown in the following that the photographs taken 4, 4.3 and 5.7 seconds later capture a representative sample of the oil drops in the water.

Referring to the 5.7 second column of Table 3, it can be seen that during this period, a 2 micron diameter oil drop rises 1.9 microns, a 100 micron drop rises 4725 microns and a 150 micron drop rises 10,633 microns. As previously indicated, the free vertical rise section of the cell to the bottom of the microscope viewing cell is a conservative 7000 microns.

Consider a zero time photograph having a 2 micron, a 10 micron and a 100 micron drop just inside the lower edge of the film image. The water sample had been stationary for 4 seconds before the photograph was taken and all oil drops had an opportunity to rise at their diameter and density determined rate for the 4 seconds. Thus, the 2 micron drop had risen 1.3 microns, the 10 micron drop 33 microns and the 100 micron drop 3316 microns. In other words, the 2 micron drop originated in a microvolume 1.3 microns below the viewing cell, the 10 micron drop in a microvolume 33 microns below the viewing cell and the 100 micron drop, 3316 microns below.

Considering the definition that all drops are uniformly dispersed, all microvolumes have equal chances of containing any drop size. It, therefore, makes no difference if the 2 micron drops originate in one microvolume and the 100 micron drops in another. All microvolumes are equivalent and the sample volume photographed will still be representative of the entire sample. This condition holds until the drop-rise distance during the static period exceeds the available path within the cell. For the system of this example, this was defined as 7000 microns and a 145.3 micron diameter oil drop will then be the cutoff point since it will rise 6992 microns in 4 seconds. Any larger drops may exceed the rise path and, even if they originated in the lowest acceptable microvolume, may have escaped the viewing cell when the photograph was taken. The microscope viewing cell limitations of this example indicate a conservative cutoff point of 100 micron diameter, and the above discussion shows that the viewing cell contains a representative sample at the end of 4 seconds and, indeed, even after 5.7 seconds, the end of the photographic cycle. The rise rate is dependent upon water density and viscosity, and oil density. Thus the actual cutoff point will change due to sample conditions for a given system.

Any system of this invention can be calibrated using procedures analogous to those summarized above.

The camera employed in this example had a 250 exposure capacity which, using three photographs per water sample, allowed photography of 80 water samples. The adequacy of this data base is dependent upon the oil content and size dispersion. Determination of the number of water samples required to capture a statistically significant number of oil drop sizes must be based on existing sample conditions for a given system.

A crystal oscillator timer with 20 millisecond resolution controlled all operations according to the timing cycle of Table 2. Such circuits may be found in "The TTL Cookbook", D. Lancaster, Howard Sams Co.

The flow control solenoid and timer were operated from a battery within the pressurized housing the Sun Pak 611 electronic flash and camera motor were operated from their internal batteries. The entire system was self-contained. Electrical operations were controlled from outside the housing by hermetically sealed switches. The entire system was integrated into a portable, self-contained fully automated apparatus capable of field use. It was enclosed in a pressurizable case and satisfied the requirements for use in National Electric Code Class 1, Division 1, Group D atmospheres. (Known explosive concentrations of hydrocarbon vapors.)

The volume of data to be manipulated made computerized reduction highly desirable. A PDP 11 system with a Summagraphics digitizer system was used. The color photograph was projected upon the platen with a vertical projection system. A Kodak 500 projector was modified to accept the double frame film strip. The film aperture was enlarged over the standard 35 mm frame to make the entire photographic image and an additional strip of surrounding unexposed film visible. Thus, the camera aperture was the image-defining mask and not the projection system. This feature allowed precise measurement of drop position within a frame. The photographs were treated in groups of three comprising a single water sample. Touching each side of an image resulted in the measurement of the diameter and the x,y location of the drop center.

For density calculations, all sharp images between 2- and 100-micron diameter were measured, stored and tabulated in the first photograph. The larger than 20 micron drops were measured in the second photo and only the 2- to 20-micron drops were included in the third. The computer rejected drops not within these limits and notified the operator. When the three photographs were digitized and tabulated, the computer selected the first drop in the data from photograph 1 and searched data from photographs 2 and 3 for a drop having a similar y-position (drop rise was in the x-axis). When one was found, the diameters were compared and, if within precision limits, density was calculated. If the density was within limits, the drop diameter and density were tabulated and stored. Override provision was available to inject operator intelligence.

Small residual water sample movement limited precision of the density determination. The effect was most noticeable on the smaller drops where the rise was only a few microns. However, the densities of many hundred drops of all sizes from all sample points were measured and no air bubbles were found. Based on this result, the decision was made, for this specific example, to measure and count all the drops in the first photograph of each time lapse triad as oil. A second program permitted total data printout, classification by drop diameter and density brackets, or calculation of ppm oil classified by drop diameter and density bracket. Density brackets were input selectable.

EXAMPLE 2

Figure 5:
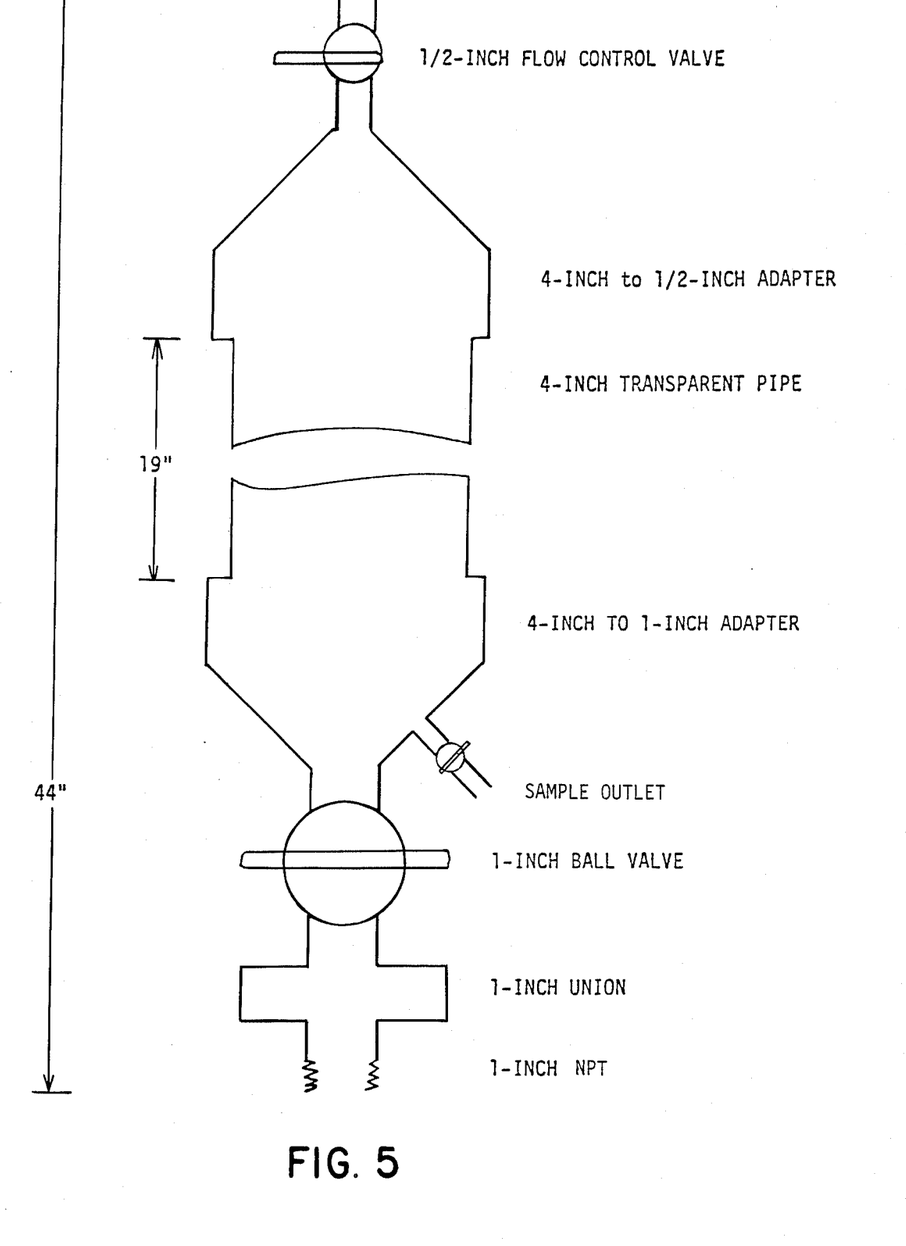
FIG. 5 schematically illustrates a sampler/separator for high oil content flows.

In some applications, the oil content of a water stream may be too high for use of the aforedescribed system which is useful, generally, for oil contents of less than 0.1%. However, to apply the system to samples taken at the inlet of the oil-water separator (often 50–60% oil), a preliminary separation was made in the sampling device shown in FIG. 5. A 6 liter cylinder was filled from the bottom with all valves open to minimize shear. After at least 30 l had passed through the cylinder, the valves were closed in anti-flow direction sequence starting at the flow control valve. Again, this minimized valve-induced shear since the liquid was stationary when the lower sample valve was closed. Pressure was released at the top valve and, after allowing separation time, the water phase was passed through the photomicrographic system at the normal rate. The separation time, sample withdrawal rate, and fluid parameters combine to fix a maximum possible drop size. Using the fluid data from Table 1 above, the equation relating static time (in minutes), $T_1$, and the number of minutes from the start of sample withdrawal, $T_2$, assumes the form of Equation 3, $$\text{Cutoff diameter in microns} = 10^4 \sqrt{\frac{1 + 11.5 \, T_2}{4.93 \times 10^4 (T_1 + T_2)}} \quad (3)$$

EXAMPLE 3

Table 4 presents the liquid parameters measured on two oil platforms on which the systems of Examples 1 and 2 were employed.

TABLE 4

| | LIQUID PARAMETERS | | |
|---|---|---|---|
| | Water Density g/ml | Water Viscosity poise | Oil Density g/ml |
| WD45C | 1.025 | 0.007 | 0.895 |
| ST177 | 1.152 | 0.00825 | 0.834 |

Sampling was taken on each platform at several sites; for Platform WD45C at "H" gunbarrel outlet, "C" gunbarrel outlet, Monosep outlet, and high oil sample at "C" gunbarrel inlet; for Platform ST177 at the separator inlet, the Wemco inlet (wall and center) and the Wemco outlet (wall and center).

The basic systems described in Examples 1 and 2 were utilized. For Platform WD45C, the transfer line between the pipeline sample valve and the standpipe pressure regulator was 5 to 15 feet of ⅜ inch ID tygon tube. (All sampling and photomicrographic work was performed on the same platform level. This decreased the total sample flowrate.) The standpipe overflow rate was not measured, but estimated at 2-3 liters per minute.

Production from two separate platforms, H and C, were separately treated on Platform C. The gunbarrel outlet streams were combined as the Monosep input. Since there was no well-mixed sampling point for the Monosep inlet, the gunbarrel outlets were photographed separately. Table 5 indicates the number of usable water sample time lapse photograph triads obtained at each sample point. In total, 2370 usable color photomicrographs were acquired on Platform WD45C.

TABLE 5

| Sample Point | Photographic Triads |
|---|---|
| H gunbarrel outlet | 254 |
| C gunbarrel outlet | 142 |
| C gunbarrel inlet | 148 |
| Monosep outlet | 246 |

Figure 6:
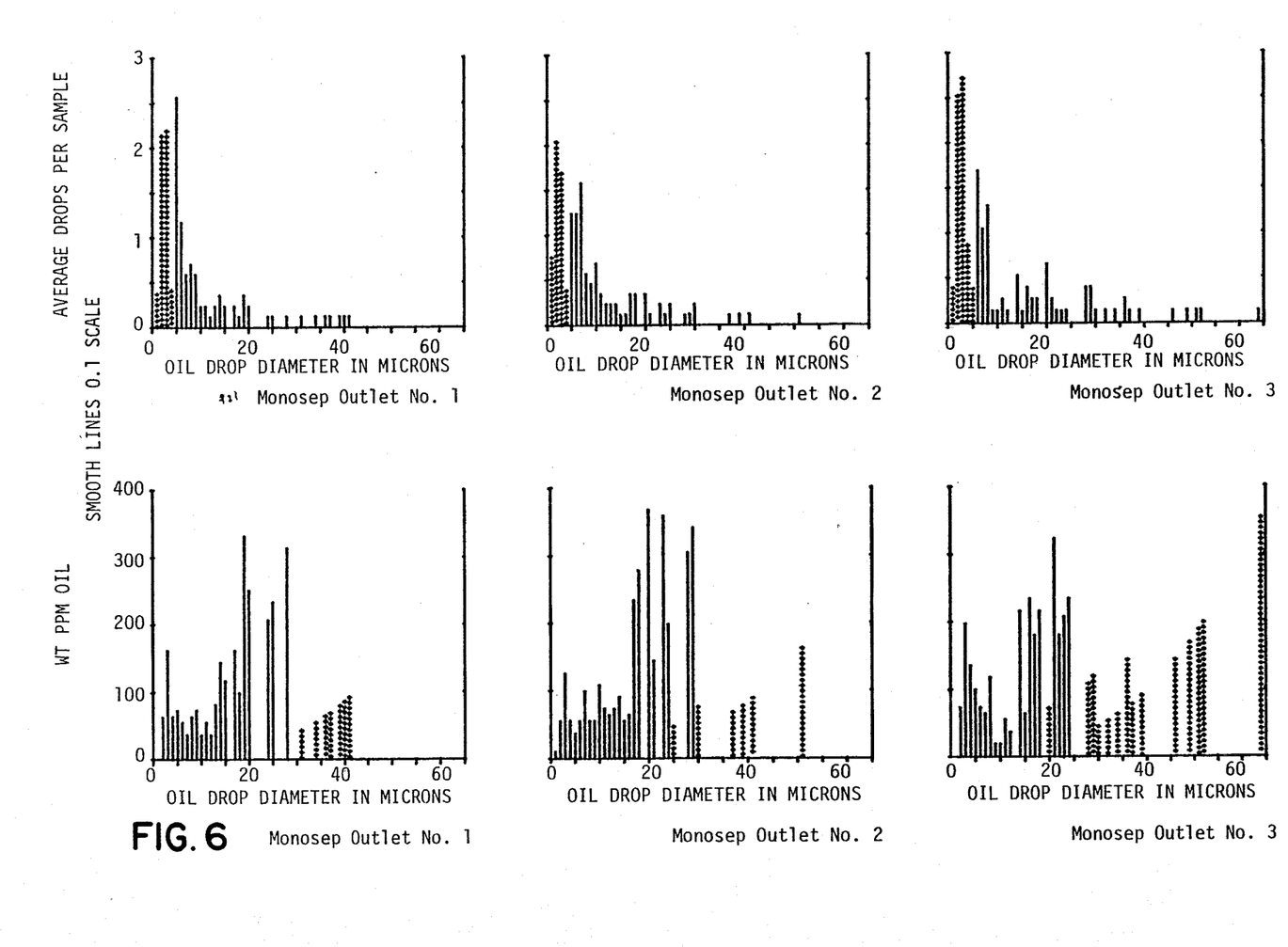
FIG. 6 is a sampling of oil parameters of a produced water flow from an off-shore well as measured by this invention.

The drops in the first photo of each water sample triad were measured and were computer-filed by film strip number and sub-ordered by water sample number. Histograms of average drops per water sample vs. size, for the composite data at each sample point, were constructed. Similarly, drops per water sample and weight ppm oil histograms were formed. Typical histograms produced for this platform are shown in FIG. 6.

Essentially the same techniques were employed for Platform ST177 including data presentation.

Table 6 presents compiled data in another form. In this format, the number of the largest drops comprising the indicated percent of the total ppm is reported, along with the smallest drop in the group. Thus the first entry means that 25% of the total ppm is generated by the seven largest drops and the smallest of the seven was 34 microns in diameter. This table provides easy evaluation of the effect of the Wemco on oil distribution by drop size.

TABLE 6

ST177, LARGEST DROPS COMPRISING INDICATED PERCENT OF TOTAL PPM

| Sample | 25% of ppm Drops | 25% of ppm Microns | 50% of ppm Drops | 50% of ppm Microns | 75% of ppm Drops | 75% of ppm Microns | Total ppm |
|---|---|---|---|---|---|---|---|
| Wemco Inlet | 7 | 34 | 28 | 22 | 153 | 10 | 734 |
| Wemco Inlet, Center | 4 | 34 | 17 | 22 | 75 | 11 | 832 |
| Wemco Inlet, Wall | 3 | 40 | 14 | 21 | 88 | 9 | 635 |
| Wemco Outlet | 2 | 31 | 8 | 15 | 161 | 5 | 84 |
| Wemco Outlet, Center | 2 | 30 | 7 | 15 | 106 | 5 | 97 |
| Wemco Outlet, Wall | 1 | 42 | 3 | 14 | 33 | 6 | 71 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A photomicrographic system for measuring the number, size distribution, and movement rate of foreign matter entities in a flowing liquid stream, comprising:
   a microscope having a field of view and an optical axis, along which lie an objective lens and a viewing lens, said microscope being disposed such that the plane of its optical axis is horizontal;
   a liquid sample cell disposed within the field of view of said microscope;
   a solenoid valve located downstream of said sample cell and connected thereto, whereby the liquid flow through the cell may be stopped or started;
   a standpipe pressure regulator fed by the flowing liquid stream and connected at its low pressure side to said sample cell, whereby a steadily flowing sample stream at essentially constant pressure is provided at the entrance of the sample cell;
   a flash illuminator disposed such that a flash therefrom illuminates said sample cell; and
   a camera disposed such that the image of said cell formed at the viewing lens of said microscope forms the film image of said camera, the latter being provided with a motor driven film winder.

2. The photomicrographic system of claim 1, further comprising electronic control means whereby the operation of said flash illuminator, said camera and its film winder, and said solenoid valve are synchronized.

3. The photomicrographic system of claim 2, wherein said electronic control means is an on-line computer.

4. The photomicrographic system of claim 2, which is housed in a portable self-contained case.

5. The photomicrographic system of claim 4, which is operable in National Electric Code Class 1, Division 1, Group D atmospheres.

6. A method of determining the number, size distribution and movement rate of foreign matter entities in a flowing liquid comprising:

permitting said flowing liquid to flow through said standpipe, cell and solenoid valve of the photomicrographic system of claim 1;

stopping the flow of said flowing liquid through said cell by closing said solenoid valve, thereby enclosing a sample of said liquid in said cell, thereby enclosing part of said sample having entrained foreign matter entities within the field of view of said microscope;

prior to the movement of the foreign matter entities to be measured from said field of view, taking a first photomicrograph of said liquid sample under the illumination of a first light flash from said flash illuminator, thereby obtaining a first photomicrograph of said foreign matter entities in that portion of said cell which is within the field of view of said microscope;

prior to the time at which the thus-photographed foreign matter entities move out of said field of view, taking at least one additional photomicrograph of said foreign matter entities, at predetermined time intervals from the taking of said first photomicrograph;

measuring the number, size and position of said foreign matter entities in said photomicrographs; and from the change in position of each of said photographed foreign matter entities during each of said predetermined time intervals as measured from said photomicrographs, determining the movement rate of each of said foreign matter entities.

7. The method of claim 6 wherein the foreign matter entities are liquid droplets.

8. A method of calculating the density of foreign matter rising droplets in a flowing liquid comprising, effecting the method of claim 7 and then, calculating the density of said photographed rising droplets from Stokes' Law.

9. A method of determining the oil content in a flowing liquid which comprises effecting the method of claim 8; from the determined density of each droplet, determining which ones are oil droplets; and from the number of thus-determined oil droplets within the field of view of the microscope and their diameters, calculating the oil content of the water sample in the sample cell.

10. The method of claim 6, wherein two of said additional photomicrographs are taken.

* * * * *